(12) United States Patent
Fjeld et al.

(10) Patent No.: US 7,040,320 B2
(45) Date of Patent: May 9, 2006

(54) VALVE DEVICE FOR CONTROLLED SUPPLY OF A PRESSURE FLUID

(75) Inventors: Anders Fjeld, Hovik (NO); Nils Terje Ottestad, Tonsberg (NO)

(73) Assignee: Techwood AS, Stavanger (NO)

(*) Notice: Subject to any disclaimer, the term of this patent is extended or adjusted under 35 U.S.C. 154(b) by 515 days.

(21) Appl. No.: 10/149,491

(22) PCT Filed: Dec. 12, 2000

(86) PCT No.: PCT/NO00/00424

§ 371 (c)(1),
(2), (4) Date: Oct. 10, 2002

(87) PCT Pub. No.: WO01/41857

PCT Pub. Date: Jun. 14, 2001

(65) Prior Publication Data

US 2003/0127098 A1    Jul. 10, 2003

(30) Foreign Application Priority Data

Dec. 13, 1999  (NO) .................................... 996167

(51) Int. Cl.
*A62B 9/02* (2006.01)

(52) U.S. Cl. ............... 128/205.24; 251/63.6; 251/84; 251/321; 251/331; 137/511

(58) Field of Classification Search ................
128/200.14–200.24, 204.18, 204.26, 205.24,
128/207.14–207.18; 251/12, 61, 62, 63.6,
251/84, 281, 318–323, 331, 336, 337, 356;
137/455, 469, 488, 511, 561 R See application file for complete search history.

(56) References Cited

U.S. PATENT DOCUMENTS 2,596,178 A * 5/1952 Seeler ................. 128/204.28

(Continued)

FOREIGN PATENT DOCUMENTS

EP      0 848 962 A2      6/1998

(Continued)

*Primary Examiner*—Glenn K. Dawson
(74) *Attorney, Agent, or Firm*—Senniger Powers

(57) ABSTRACT

A valve device for controlled supply of a pressure fluid, having a housing (2) with a supply chamber (3) for the supply of a pressure fluid from an inlet (4) connected to a pressure fluid source, and having an outlet (5) communicating with the supply chamber (3) via an outlet valve (6). The valve device includes a reference chamber (10) connected to the outlet (5) through a narrow, leakage-forming duct (11), a regulating unit (12–14) adapted to keep the supply chamber (3) permanently pressurised at a value just above the pressure in the reference chamber (10), and a control valve (20) having a valve body (21) for opening and closing of a passage (19) between the supply chamber (3) and the reference chamber (10). The control valve body (21) is arranged to be influenced by an external force for opening of the passage (19), and to be influenced by a closing force determined by the pressure in the chambers (3, 10) at the cessation of the influence of the external force, and the outlet valve (6) is a one-way valve having a predetermined opening pressure.

24 Claims, 2 Drawing Sheets

U.S. PATENT DOCUMENTS

| | | | |
|---|---|---|---|
| 4,054,133 A | * 10/1977 | Myers | 128/204.26 |
| 4,575,042 A | 3/1986 | Grimland et al. | |
| 4,667,670 A | 5/1987 | Feathers | |
| 4,971,049 A | 11/1990 | Rotariu et al. | |
| 5,360,000 A | * 11/1994 | Carter | 128/204.26 |
| 5,464,009 A | 11/1995 | Tatarek-Gintowt | |
| 5,666,945 A | 9/1997 | Davenport | |
| 5,881,725 A | * 3/1999 | Hoffman et al. | 128/204.26 |
| 6,752,152 B1 | * 6/2004 | Gale et al. | 128/204.26 |

FOREIGN PATENT DOCUMENTS

| | | |
|---|---|---|
| EP | 0 848 962 A3 | 6/1998 |
| NO | 176078 | 1/1995 |
| NO | 953703 | 9/1995 |

* cited by examiner

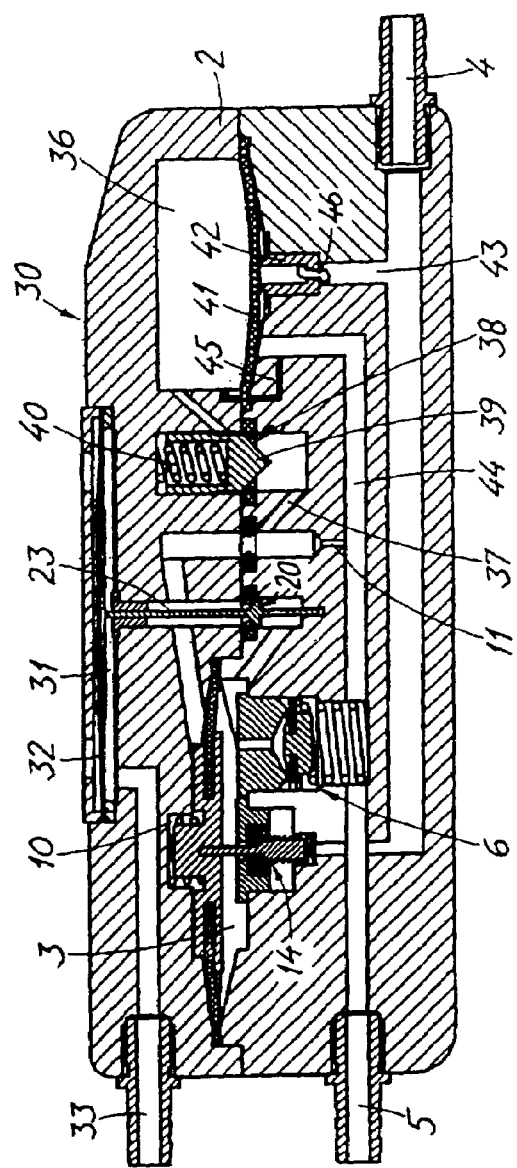

VALVE DEVICE FOR CONTROLLED SUPPLY OF A PRESSURE FLUID

BACKGROUND OF THE INVENTION

A valve device for controlled supply of a pressure fluid. The invention relates to a valve device for controlled supply of a pressure fluid, comprising a housing having a supply chamber for the supply of a pressure fluid from an inlet connected to a pressure fluid source, and having an outlet communicating with the supply camber via an outlet valve.

The present valve device in the first place has been developed with the view of functioning as a breathing-controlled valve which is to give persons having a lung failure a contribution of oxygen.

A considerable number of persons having a lung failure are dependent on their breathing air being enriched with oxygen. This primarily takes place in that the patients are equipped with a portable pressure reservoir and are supplied with oxygen via a nose catheter. In most cases the oxygen is supplied as a continuous flow, and the patient consequently misses the oxygen quantity supplied during the time in which the patient himself does not inhale. In practice this implies that approximately ⅔ of the supplied oxygen is lost. In addition, the constant gas flow into the nostrils will be unpleasant to most people because the mucous membranes of the nose become dry and irritated. On a global basis there is a very large number of persons which receive a supply of oxygen from a portable reservoir (approximately 800,000 in the U.S.). The yearly costs of oxygen to the individual patient is of the order of NOK 100,000,. Thus, one can achieve large savings by minimising the oxygen loss.

Today, there are delivered electronic oxygen savers which are able to record the starting time for each inhalation, and which also provide for a metered supply of oxygen. These are based on electronic pressure sensors, and are constructed to deliver oxygen in a certain (adjustable) time interval after that start of inhalation has been recorded. Thus, if the patient has an irregular breathing pattern, one will constantly run the risk that a part of the supplied oxygen never arrives at the lungs of the user. The drawback of these oxygen savers is that the batteries must be changed relatively often, and that they are complicated and expensive. So far, these have not been a success in the market.

An oxygen saver should have a quick response and, ideally, should deliver oxygen only as long as the patient inhales. This implies that the oxygen saver must be able to register the pressure in the breathing passages of the patient independently of whether the oxygen saver delivers oxygen or not. In addition, if the oxygen saver is to be able to be based on a pure mechanical regulation of the oxygen flow, the control device for the oxygen supply must be so sensitive that it can be controlled by the small pressure forces which will be generated in the nose catheter by the respiration of the patient.

SUMMARY OF THE INVENTION

The object of the invention is to provide a valve device which, by the influence of a particularly small external force, is able to open for the supply of a pressure fluid, and thus is very well suited for a respiration-controlled supply of a contribution of oxygen to persons having a lung failure.

The above-mentioned object is achieved with a valve device of the introductorily stated type which, according to the invention, is characterised in that it comprises a reference chamber connected to the outlet through a narrow, leakage-forming duct, a regulating unit seeing to it that the supply chamber is kept permanently pressurised at a value just above the pressure in the reference chamber, and a control valve having a valve body for opening and closing of a passage between the supply chamber and the reference chamber, the valve body being arranged to be influenced by an external force for opening of the passage, and to be influenced by a closing force determined by the pressure in said chambers at the cessation of the external force influence, the outlet valve being a one-way valve having a predetermined opening pressure.

An advantageous embodiment of the valve device, resulting in a very small force requirement for activation of the device, is characterised in that the valve body of the control valve comprises a cylindrical thin rod which is carried approximately leakage-free and frictionless in a guide in the valve device housing.

Another embodiment of the valve device, which is designed for demand-controlled supply of oxygen to the respiration of a user, is characterised in that it comprises a sensor chamber which is partly defined by a sensor diaphragm arranged to sense the breathing pressure of the user, the sensor diaphragm being operatively connected to the valve body of the control valve, so that the passage between the supply chamber and the reference chamber is opened when a negative pressure is generated in the sensor chamber by the inhalation of the user.

When the small pressure forces which will be generated in a nose catheter by the respiration of a user, actuate a sensor diaphragm of the stated design and of a suitable size, the forces will be of the order of 1–2 kiloponds. With the valve device according to the invention one has managed to minimise the regulating forces to a sufficient degree by seeing to it that the flow-regulating element is influenced by very small forces irrespective of weather the device is in the open or in the closed position.

BRIEF DESCRIPTION OF THE DRAWINGS

The invention will be further described below in connection with exemplary embodiments with reference to the drawings, wherein

FIG. 2 shows a sectional view corresponding to that of FIG. 1, wherein the valve device is designed for use as an oxygen saver; and FIG. 3 shows the oxygen saver connected to a nose catheter.

DETAILED DESCRIPTION OF THE PREFERRED EMBODIMENTS

Figure 1:
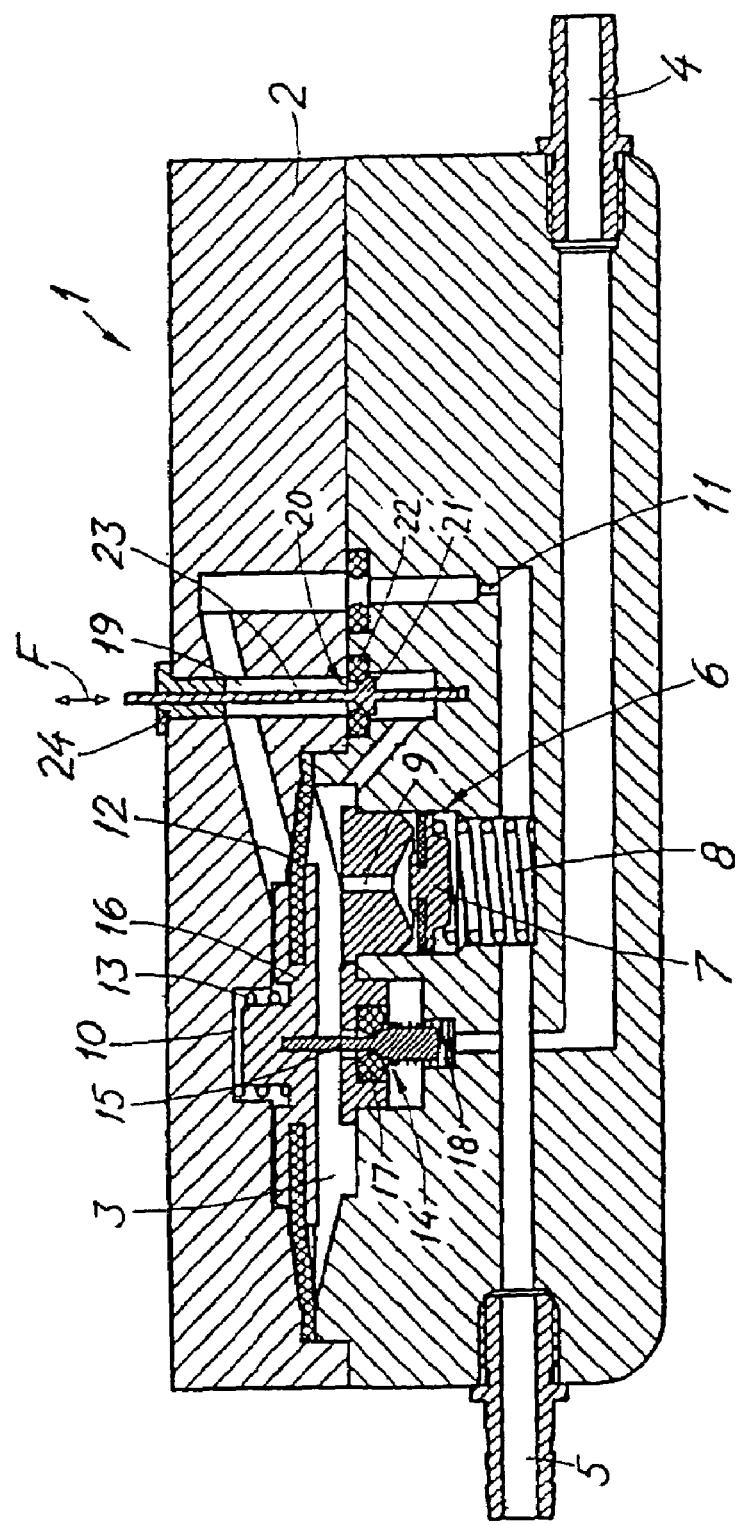
FIG. 1 shows a sectional view of a valve device according to the invention.

The valve device 1 shown in FIG. 1 comprises a housing 2 in which there is arranged a supply chamber 3 for the supply of a pressure fluid from an inlet 4 which, in use, will be connected to a pressure fluid source (designated by 25 in FIG. 3). The supply chamber 3 communicates with an outlet 5 via an outlet valve which is in the form of a one-way valve 6. The valve comprises a valve body 7 which is influenced by a spring 8 in the direction towards the closed position of the valve, so that the valve opens at a definite opening pressure in the supply chamber. Fluid flow through the valve in the illustrated embodiment takes place via a relatively narrow passage 9.

In the housing 2 there is further provided a reference chamber 10 which is connected to the outlet 5 via a narrow, leakage-forming duct 11. A regulating unit sees to it that the supply chamber 3 is kept permanently pressurised at a value lying just above the pressure in the reference chamber 10. This unit comprises a diaphragm 12 forming a partition between the supply chamber and the reference chamber, a prestressed spring 13 arranged in the reference chamber, which sping influences the diaphragm 12 and provides for the desired permanent pressure difference (e.g. 10 mbar) between the chambers, and a supply valve arranged between the supply chamber 3 and the inlet 4 and having a valve body 15 which is operatively connected to the diaphragm 12. As shown, the diaphragm comprises a pressure plate 16 in its central region, and this is centrally connected to the valve body 15. The valve body cooperates with a valve seat formed on an O-ring 17. At the end of the valve body 15 located at a distance from the diaphragm 12, this body is influenced by a return spring 18.

The reference chamber 10 is connected to the supply chamber 3 via a passage 19. In this passage there is arranged a control valve 20 having a valve body 21 which cooperates with a seat formed on an O-ring 22. The valve body is arranged as an enlarged part of a cylindrical thin rod 23 which is guided approximately leakage-free and frictionless through a guide 24 to the outside of the housing 2. Thus, the passage 19 may be opened in that the valve body 21 is influenced by an external force, at the same time as the valve body will be influenced by a closing force which is determined by the pressure in the chambers 3, 10 at the cessation of the influence of the external force. The closing force, which is due to the pressure influence at the lower end of the rod 23, will be very small because of the small cross-section of the rod. Said opening force and the closing force in FIG. 1 are symbolised by the double-headed arrow F.

The operation of the valve device will be further described below.

When the valve device is in the closed position, the supply camber 3 is permanently pressurised by means of the regulating unit 12–14 to a value lying just above the pressure in the reference camber 10. This pressure will be determined by the prestressing of the spring 13 and the pressure in the reference chamber. At the starting point the reference chamber 10 has the same pressure as the surrounding atmosphere, since the chamber communicates with the outlet 5 via the leakage-forming duct 11. In this situation the pressure in the supply chamber 3 is not sufficiently high to open the one-way valve 6.

The control valve body 21 is kept in the closed position against its seat 22 because of the pressure difference between the supply chamber and the reference chamber. When the control valve body is pressed away from its seat by the application of an external force, an open connection is established between these two chambers. This entails that the pressure rises quickly both in the reference chamber and in the supply chamber, so that the one-way valve 6 at a certain pressure opens for the delivery of pressure fluid from the valve device via the outlet 5. The passage 9 through the one-way valve is constricted, so that it is required that the pressure in the supply chamber 3 must have a value closely up towards the pressure in the inlet 4 for optimum through-flow.

When the pressure rises in the two chambers 3 and 10, a somewhat larger force will be required to keep the control valve 20 open. However, the force demand is still modest because of the small cross-section of the control valve rod 23 at the guide 24. When the external force influence on the control valve body 21 ceases, the pressure in the supply chamber will see to it that the control valve body 21 returns quickly to its seat. This entails that the pressure in the reference chamber 10 is quickly ventilated via the duct 11. Thereby also the pressure in the supply chamber 3 drops, and the one-way valve 6 closes for through-flow.

FIG. 2 shows an embodiment of the valve device wherein this is designed for use as an oxygen saver, i.e. as a devise for demand-controlled supply of oxygen to the respiration of a user.

The oxygen saver 30 comprises the same structural elements as those forming part of the embodiment described above, and which are designated by the same reference numerals, and besides some additional elements which will be described below.

As shown, the hosing 2 comprises a sensor chamber 31 which is partly defined by a sensor diaphragm 32, the sensor chamber being connected to a second inlet 33 which, in use, will be connected to a hose as shown in FIG. 3, for the supply of the user's breathing pressure to the sensor chamber. Thus, the sensor diaphragm 32 is arranged to sense the user's breathing pressure, the diaphragm, at the side facing away from the sensor chamber, being ventilated towards the surrounding atmosphere. In its central region the sensor diaphragm 32 is connected to the valve body of the control valve 20 via the rod 23, so that the passage between the supply chamber 3 and the reference chamber 10 is opened when a negative pressure is produced in the sensor chamber 31 at the users inhalation.

The operation of the oxygen saver is as described above, but the valve device in the illustrated embodiment is also provided with a safety means in the form of a pneumatic time switch causing the valve device to go to open position for the supply of a continuous oxygen flow to the user or patient if the breathing pressure is not registered in the course of a predetermined time period, e.g. of approximately 20 seconds.

The safety means comprises a pressure chamber 36 arranged in the housing 2 and connected to the supply chamber 3 via a passage 37 containing a one-way valve 38 having a valve body 39 which is influenced by a prestressed spring 40 in the direction towards the closed position of the valve. The pressure chamber 36 is partly defined by a resilient disc 41 which, in its central region, at the side facing away from the camber, is arranged to cooperate with a seat ring 42 placed in a passage 43 leading to the outlet 4. When the disc 41 is raised from the seat ring 42, the passage 43 is brought into connection with an additional passage 44 connected to the outlet 5. The pressure chamber 36 is connected to the passage 44 leading to the outlet 5 via a narrow passage 45, so that a permanent small leakage is provided from the chamber 36 to the outlet.

The function of the safety means is based on the pressure in the supply chamber 3 rising to approximately the same value as the supply pressure for the oxygen each time the oxygen saver is activated. This pressure is transferred to the pressure chamber 36 via the one-way valve 38, something causing the resilient disc 41 to be pressed down towards the seat ring 42 and thereby to close the passage 43, 44 between the inlet 4 and the outlet 5 via the seat ring 42. The permanent leakage between the pressure chamber 36 and the outlet 5 via the narrow passage 45 entails that the camber constantly must be supplied with oxygen via the one-way valve 38 if the disc 41 is to manage to maintain the sealing force against the seat ring 42. Consequently, the valve device will provide for a continuous through-flow of oxygen if the patient has not breathed in the course of the chosen predetermined time period. The level of this through-flow is determined by a flow restriction 46 in the seat ring 42.

The return spring 40 for the valve body 39 of the one-way valve 38 has a modest prestressing. The pressure in the camber 36 therefore, each time the oxygen saver is activated by the respiration of the patient, will rise closely up towards the pressure in the inlet 4. An important safety detail is that the oxygen saver must not be allowed to adjust itself to a position in which the patient is not supplied with oxygen. The resilient disc 41 therefore will be arranged to shut off the passage between the inlet 4 and the outlet 5 only when the pressure in the pressure chamber 36 is higher than the opening pressure of the one-way valve 6.

FIG. 3 shows the oxygen saver 30 connected to a nose catheter 47 for the supply of oxygen to the relevant user or patient. As appears, the inlet 33 of the sensor chamber is connected to a first hose 48 leading to one side of the nose catheter 47, whereas the outlet 5 of the oxygen saver is connected to a second hose 49 leading to the other side of the nose catheter. The desired properties is achieved in that the hose 48 functions as a pure sensing line seeing to it that the valve device is activated by the negative pressure arising when the user inhales, whereas the second hose 49 functions as a supply line for oxygen delivered by the oxygen saver. This causes the oxygen saver to be able to deliver gas only as long as the user is in the inhalation phase.

The invention claimed is:

1. A valve device for controlled supply of a pressure fluid, comprising a housing (2) having a supply chamber (3) for the supply of a pressure fluid from an inlet (4) connected to a pressure fluid source, and having an outlet (5) communicating with the supply chamber (3) via an outlet valve (6), characterised in that the valve device comprises a reference chamber (10) connected to the outlet (5) through a narrow, leakage-forming duct (11), a regulating unit (12–14) adapted to keep the supply chamber (3) permanently pressurised at a value just above the pressure in the reference chamber (10), and a control valve (20) having a valve body (21) for opening and closing of a passage (19) between the supply chamber (3) and the reference chamber (10), the valve body (21) being arranged to be influenced by an external force for opening of the passage (19), and to be influenced by a closing force determined by the pressure in said chambers (3,10) at the cessation of the external force influence, the outlet valve (6) being a one-way valve having a predetermined opening pressure.

2. A valve device according to claim 1, characterised in that the regulating unit comprises a diaphragm (12) forming a partition between the supply chamber (3) and the reference chamber (10), a spring (13) arranged in the reference chamber (10), which spring actuates the diaphragm (12) and provides for a desired pressure difference between the chambers (3,10), and a supply valve (14) arranged between the supply chamber (3) and the inlet (4) and having a valve body (15) which is operatively connected to the diaphragm (12), so that the supply valve (14) is opened and closed in step with the opening and closing of the control valve (20).

3. A valve device according to claim 2, characterised in that the valve body (21) of the control valve (20) comprises a cylindrical thin rod (23) which is carried approximately leakage-free and frictionless in a guide (24) in the valve device housing (2).

4. A valve device according to claim 2, for demand-controlled supply of oxygen to the respiration of a user, characterised in that it comprises a sensor chamber (31) which is partly defined by a sensor diaphragm (32) arranged to sense the breathing pressure of the user, the sensor diaphragm (32) being operatively connected to the valve body (21) of the control valve (20), so that the passage (19) between the supply chamber (3) and the reference chamber (10) is opened when a negative pressure is produced in the sensor chamber (31) at the user's inhalation.

5. A valve device according to claim 4, characterised in that the safety means comprises a pressure chamber (36) which is connected to the supply chamber (3) via a passage (37) having a one-way valve (38), which pressure chamber (36) is partly defined by a resilient disc (41) shutting off the passage (43, 44) between the inlet (4) and the outlet (5) when the pressure in the pressure chamber (36) is close to the supply pressure of the pressure fluid source (25), the pressure chamber being connected to the outlet (5) via a narrow, leakage-forming passage (45), so that the resilient disc (41) opens the passage (43, 44) between the inlet and the outlet if the pressure chamber (36) is not supplied with oxygen from the outlet chamber (3) in the course of the predetermined time period.

6. A valve device according to claim 5, characterised in that the resilient disc (41) is arranged to shut off the passage (43, 44) between the inlet (4) and the outlet (5) only when the pressure in the pressure chamber (36) is higher than the opening pressure of the outlet valve (6).

7. A valve device according to claim 6, characterised in that a flow restriction (46) is arranged in the passage (43, 44) between the inlet (4) and the outlet (5).

8. A valve device according to claim 5, characterised in that a flow restriction (46) is arranged in the passage (43, 44) between the inlet (4) and the outlet (5).

9. A valve device according to claim 1, characterised in that the valve body (21) of the control valve (20) comprises a cylindrical thin rod (23) which is carried approximately leakage-free and frictionless in a guide (24) in the valve device housing (2).

10. A valve device according to claim 9, characterised in that it comprises a safety means (36–38, 41–45) which is arranged to open a passage (43, 44) between the inlet (4) and the outlet (5) if the breathing pressure of the user is not registered by the valve device (1) during a predetermined time period.

11. A valve device according to claim 10, characterised in that the safety means comprises a pressure chamber (36) which is connected to the supply chamber (3) via a passage (37) having a one-way valve (38), which pressure chamber (36) is partly defined by a resilient disc (41) shutting off the passage (43,44) between the inlet (4) and the outlet (5) when the pressure in the pressure chamber (36) is close to the supply pressure of the pressure fluid source (25), the pressure chamber being connected to the outlet (5) via a narrow, leakage-forming passage (45), so that the resilient disc (41) opens the passage (43,44) between the inlet and the outlet if the pressure chamber (36) is not supplied with oxygen from the outlet chamber (3) in the course of the predetermined time period.

12. A valve device according to claim 11, characterised in that the resilient disc (41) is arranged to shut off the passage (43,44) between the inlet (4) and the outlet (5) only when the pressure in the pressure chamber (36) is higher than the opening pressure of the outlet valve (6).

13. A valve device according to claim 12, characterised in that a flow restriction (46) is arranged in the passage (43, 44) between the inlet (4) and the outlet (5).

14. A valve device according to claim 11, characterised in that a flow restriction (46) is arranged in the passage (43, 44) between the inlet (4) and the outlet (5).

15. A valve device according to claim 10, characterised in that a flow restriction (46) is arranged in the passage (43, 44) between the inlet (4) and the outlet (5).

16. A valve device according to claim 9, for demand-controlled supply of oxygen to the respiration of a user, characterised in that it comprises a sensor chamber (31) which is partly defined by a sensor diaphragm (32) arranged to sense the breathing pressure of the user, the sensor diaphragm (32) being operatively connected to the valve body (21) of the control valve (20), so that the passage (19) between the supply chamber (3) and the reference chamber (10) is opened when a negative pressure is produced in the sensor chamber (31) at the user's inhalation.

17. A valve device according to claim 16, characterised in that the safety means comprises a pressure chamber (36) which is connected to the supply chamber (3) via a passage (37) having a one-way valve (38), which pressure chamber (36) is partly defined by a resilient disc (41) shutting off the passage (43, 44) between the inlet (4) and the outlet (5) when the pressure in the pressure chamber (36) is close to the oxygen supply pressure, the pressure chamber being connected to the outlet (5) via a narrow, leakage-forming passage (45), so that the resilient disc (41) opens the passage (43, 44) between the inlet and the outlet if the pressure chamber (36) is not supplied with oxygen from the outlet chamber (3) in the course of the predetermined time period.

18. A valve device according to claim 17, characterised in that the resilient disc (41) is arranged to shut off the passage (43, 44) between the inlet (4) and the outlet (5) only when the pressure in the pressure chamber (36) is higher than the opening pressure of the outlet valve (6).

19. A valve device according to claim 18, characterised in that a flow restriction (46) is arranged in the passage (43, 44) between the inlet (4) and the outlet (5).

20. A valve device according to claim 17, characterised in that a flow restriction (46) is arranged in the passage (43, 44) between the inlet (4) and the outlet (5).

21. A valve device according to claim 1, for demand-controlled supply of oxygen to the respiration of a user, characterised in that it comprises a sensor chamber (31) which is partly defined by a sensor diaphragm (32) arranged to sense the breathing pressure of the user, the sensor diaphragm (32) being operatively connected to the valve body (21) of the control valve (20), so that the passage (19) between the supply chamber (3) and the reference chamber (10) is opened when a negative pressure is produced in the sensor chamber (31) at the user's inhalation.

22. A valve device according to claim 21, characterised in that the sensor chamber (31) and the outlet (5) of the valve device are connected to respective hoses (48 resp. 49) leading to a nose catheter (47) for the user, so that the hose (48) from the sensor chamber (31) is a sensing line conveying negative pressure at the users inhalation, and the hose (49) from the outlet (5) supplies oxygen to the user during the inhalation phase thereof.

23. A valve device according to claim 22, characterised in that it comprises a safety means (36–38, 41–45) which is arranged to open a passage (43, 44) between the inlet (4) and the outlet (5) if the breathing pressure of the user is not registered by the valve device (1) during a predetermined time period.

24. A valve device according to claim 21, characterised in that it comprises a safety means (36–38, 41–45) which is arranged to open a passage (43, 44) between the inlet (4) and the outlet (5) if the breathing pressure of the user is not registered by the valve device (1) during a predetermined time period.

* * * * *